United States Patent [19]

Bakos et al.

[11] Patent Number: 5,072,022
[45] Date of Patent: Dec. 10, 1991

[54] NOVEL HERBICIDE COMPOSITION

[75] Inventors: József Bakos; Bálint Heil; Imre Toth; Béla Édes, all of Veszprém; István Gebhardt, Budapest; Ferenc Bihari, Budapest; Anna Durkónée Pónácz, Budapest; Gyula Eifert, Dunaharaszti; Jenö Király, Budapest; Éva Konok née Horváth, Budapest; László Lukács, Budapest; Agnes Mészáros née Szekrényesi, Budapest; Béla Radvány, Budapest; Lajos Sárosi, Budapest, all of Hungary

[73] Assignee: Budapest Vegyimuvek, Budapest, Hungary

[21] Appl. No.: 454,779

[22] Filed: Dec. 21, 1989

[30] Foreign Application Priority Data

Dec. 27, 1988 [HU] Hungary .............................. 6610/88

[51] Int. Cl.⁵ ............................................ C07C 69/76
[52] U.S. Cl. ........................................ 560/65; 71/107
[58] Field of Search ............................ 560/65; 71/107

[56] References Cited
FOREIGN PATENT DOCUMENTS
2463119 2/1981 France .
2137988 10/1984 United Kingdom .

Primary Examiner—Paul J. Killos
Attorney, Agent, or Firm—Herbert Dubno; Jonathan Myers

[57] ABSTRACT

The invention relates to a novel herbicide composition, which comprises the (S) enantiomer or racemate of a compound of the general formula (I),

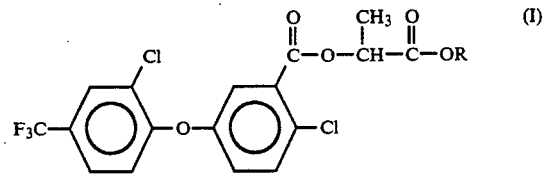

wherein R stands for a methyl or ethyl group, as active ingredient in an amount of 0.01 to 95% by weight together with one or more solid and/or liquid carrier(s), preferably grist(s) of native or synthetic material(s) and/or with inert solvents(s), preferably xylene(s) and/or cyclohexanone; and optionally with surface active agents(s), preferably anionic and/or nonionic emulsifying or dispersing agent(s).

The invention further relates to the above compounds of the general formula (I) as well as to a process for the preparation thereof.

The compounds according to the invention possess an outstanding herbicidal effect (over 90%) and advantageous selectivity threshold values against cultivated plants.

11 Claims, No Drawings

NOVEL HERBICIDE COMPOSITION

FIELD OF THE INVENTION

This invention relates to the herbicidally active (S)- and (RS)-1'-alkoxycarbonylethyl 2-chloro-5-(2-chloro-4-trifluoromethylphenoxy)benzoates of the formula (I),

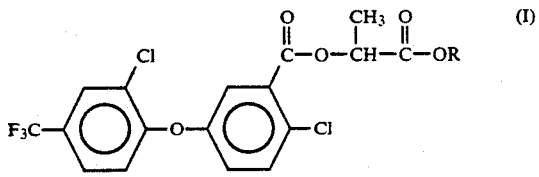

wherein R stands for a methyl or ethyl group and which have not been described in the literature.

The invention further relates to herbicide compositions containing as active ingredients (S)- or (RS)-1'-alkoxycarbonylethyl 2-chloro-5-(2-chloro-4-trifluoromethylphenoxy)benzoates of the formula (I), wherein R stands for a methyl or ethyl group as well as to a process for the preparation of the active ingredients of the formula (I).

Thus, the invention relates to the following four compounds:

(S)-1'-methoxycarbonylethyl 2-chloro-5-(2-chloro-4-trifluoromethylphenoxy)benzoate (compound No. 1);

(RS)-1'-methoxycarbonylethyl 2-chloro-5-(2-chloro-4-trifluoromethylphenoxy)benzoate (compound No. 2);

(S)-1'-ethoxycarbonylethyl 2-chloro-5-(2-chloro-4-trifluoromethylphenoxy)benzoate (compound No. 3); and (RS)-1'-ethoxycarbonylethyl 2-chloro-5-(2-chloro-4-trifluoromethylphenoxy)benzoate (compound No. 4).

BACKGROUND OF THE INVENTION

Substituted diphenyl ether derivatives of the formula (I),

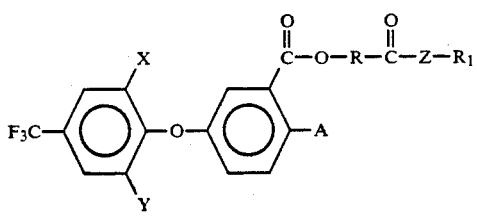

wherein
A stands for halogen or a cyano group;
X stands for hydrogen or halogen;
Y stands for hydrogen or halogen;
Z stands for oxygen or sulfur;
R stands for a $C_{1-3}$alkylene group substituted by a $C_{1-4}$alkyl group; and
$R_1$ stands for a $C_{1-10}$alkyl group
are described in the German patent specification (DE-PS) No. 3,029,728.

Although the compounds of the formula (I) according to the present invention are within the scope of the formula (1) of the German patent specification (DE-PS) No. 3,029,728, only a single compound namely, (RS)-1'-ethoxycarbonylethyl 2-bromo-5-(2-chloro-4-trifluoromethylphenoxy)benzoate is disclosed in the patent specification cited above.

Neither the (S)-enantiomers nor racemates of the compounds according to the present invention, nor their preparation, physical and chemical characteristics and herbological properties are defined in the patent specification cited above. Thus, these compounds have not been prepared and are therefore novel.

There is a constant demand for novel compounds capable of inhibiting the development of an undesired vegetation. The principal aim of the research consists in the selective inhibition of the development of weeds in the most frequent cases such as wheat, maize, rice soy bean or cotton. The uncontrolled growth of weeds is accompanied by a significant loss of production whereby the gain of the grower (farmer) is lowered and the expenses of the consumer become higher.

DESCRIPTION OF THE INVENTION

It has been found in the course of our herbological (plant protective) investigations that the compounds according to the present invention possess a substantially higher herbicidal activity and selectivity than those of analogous compounds known heretofore. The structurally related (RS)-1'-ethoxycarbonylethyl 2-bromo-5-(2-chloro-4-trifluoromethylphenoxy)benzoate (compound A) and the commercially available (RS)-1'-ethoxycarbonylethyl 5-(2-chloro-4-trifluoromethylphenoxy)-2-nitrobenzoate (compound B, see the published European patent application No. 0,020,052 A1) furthermore the R-antipodes of the compounds relating to present invention, (R)-1'-methoxycarbonylethyl 2-chloro-5-(2-chloro-4-trifluoromethylphenoxy)benzoate (compound C) and (R)-1'-ethoxycarbonylethyl 2-chloro-5-(2-chloro-4-trifluoromethylphenoxy)benzoate (compound D) were used as reference (standard) substances in these examinations.

It has surprisingly been found in the course of our in-depth (detailed) investigations that the herbicidal activity (in terms of doses required to achieve a herbicidal effect over 90%) of the four compounds according to the invention (i.e. compounds Nos. 1 to 4) is 3 to 10 times as strong as that of the compounds A, B, C and D (see Table 1) and their selectivity threshold values are 2 to 4 times higher than those of the compounds A, B, C and D (see Table 2), while the doses required to a herbicidal efficiency over 90% (Table 1) and the selectivity threshold values relating to the individual weeds and cultivated plants (Table 2) of the compounds A, B, C and D) are close to one another. The definition and symbols of the weeds (a to f) and cultivated plants (g to j), respectively are given in Example 10.

Our invention is the more surprising since the selectivity threshold values of the compounds A, B, C and D approximate the herbicidal effect over 90%, whereby the weed-killing by the compounds A, B, C and D in cultivated plants becomes doubtful.

The much higher efficiency of the compounds Nos. 1 to 4, substituted by a chlorine in 2-position, in comparison to the compounds substituted by a nitro group is particularly surprising and unexpected for a person skilled in the art.

The biological results of the compounds according to present invention represent a valuable contribution to the present state of art from the point of view that the doses (g/ha) required to achieve a herbicidal effect over 90% amount in the case of the (RS) compound to a 1.5 to 3 times higher value, in the case of the (R)-antipode to a 3 to 10 times higher value than that of the (S)-antipode. We have found to our surprise that the doses required to achieve a herbicidal effect over 90% rise to meet the selectivity threshold value for the (R)-antipodes, for this reason (R)-antipodes not to be used as herbicides in cultivated plants.

By knowing the herbicidal activity and the selectivity threshold value of compounds No. 1, 2, 3 and 4 according to the present invention - especially on the basis of the herbological behavior of the compounds A, B, C and D - it can be stated, that the outstanding herbicidal activity and selectivity threshold value of compounds No. 1, 2, 3 and 4 according to the present invention, and the superior suitability of those compounds resulting from the interrelation of both above mentioned characteristics, which were unexpected for a person skilled in the art, have not been recognized during the investigation of compounds of similar structure.

The compounds of the formula (I)(, wherein R stands for a methyl or ethyl group, can be prepared by known methods, e.g. by
a) reacting the (S) enantiomer or racemate of a lactic acid ester of the formula (II),

wherein R is a methyl or ethyl group, with an at least stoichiometric amount of a 2-chloro-5-(2-chloro-4-trifluoromethylphenoxy)benzoyl halide, preferably the chloride, suitably in the presence of an acid binding agent; or
b) reacting the (S) enantiomer or racemate of an alkyl 2-halopropionate of the formula (III),

wherein R stands for a methyl or ethyl group and Hal is chlorine or bromine, with 2-chloro-5-(2-chloro-4-trifluoromethylphenoxy)benzoic acid, preferably in the presence of an aza-compound, such as 1,5-diazabicyclo[5.4.0]undec-5-ene (DBU).

Any inert solvent may be used in the above reactions. Suitable solvents are e.g.: pentane, hexane, heptane, cyclohexane, petroleum ether, gasoline, ligroine, benzene, toluene xylene, dichloromethane, dichloroethan, chloroform, carbon tetrachloride, chlorobenzene, o-dichlorobenzene, diethyl ether, dibutyl ether, ethylene glycol, dimethyl ether, tetrahydrofuran, dioxane, acetone, methyl ethyl ketone, methyl isopropyl ketone, methyl isobutyl ketone, methyl acetate, ethyl acetate, acetonitrile, propionitrile, dimethylformamide (DMF), N-methylpyrrolidone, dimethyl sulfoxide (DMSO), tetramethylene sulfone or hexamethylphosphoric acid triamide.

Hydroxides, hydrogen carbonates, carbonates and alkoxides of alkaline metals as well as aliphatic, aromatic or heterocyclic amines are useful acid binding agents.

According to a preferred embodiment of the process of the present invention, approximately equimolar amounts of the starting substances are reacted at a temperature between −20° C. and the boiling point of the reaction mixture. Preferably, a solution of 2-chloro-5-(2-chloro-4-trifluoromethylphenoxy)benzoic acid or its acid chloride is added portionwise at a temperature between −20° C. and 35° C. and after this addition, the reaction mixture is stirred under reflux up to the desired progress of the reaction (transformation). After cooling down, the solution is washed with dilute acid, then dilute base and water and the phases are separated. The product can be obtained in any known way, e.g. by evaporation.

The invention further relates to a herbicide composition containing the (S) enantiomer or racemate of a compound of the formula (I), wherein R stands for a methyl or ethyl group, as active ingredient in an amount of 0.01 to 95% by weight together with one or more solid and/or liquid carriers, preferably grists of native or synthetic materials and/or with inert solvents, preferably xylenes and/or cyclohexanone; and optionally with surface active agents, preferably anionic and/or nonionic emulsifying or dispersing agents.

According to another aspect of the invention, there is provided a process for the preparation of the (S) enantiomers or racemates of the compounds of the formula (I), wherein R stands for a methyl or ethyl group, which comprises
a) reacting the (S) enantiomer or racemate of a lactic acid ester of the formula (II), wherein R is a methyl or ethyl group, with 2-chloro-5-(2-chloro-4-trifluoromethylphenoxy)benzoyl halide, preferably the chloride in a solvent, preferably in the presence of an acid binding agent; or
b) reacting the (S) enantiomer or racemate of an alkyl 2-halopropionate, preferably of alkyl 2-bromopropionate of the formula (III), where R is a methyl or ethyl group and Hal is chlorine or bromine, with 2-chloro-5-(2-chloro-4-trifluoromethylphenoxy)-benzoic acid in a solvent, suitably in the presence of an aza-compound, preferably in the presence of 1,5-diazabicyclo[5.4.0]undec-5-ene (DBU), then separating the (S) enantiomer or racemate of the thus obtained compound of the formula (I), wherein R stands for a methyl or ethyl group, from the reaction mixture in a known manner, resolving, if desired, the racemate of a compound of the formula (I), wherein R stands for a methyl or ethyl group, in a known way and optionally purifying the (S) enantiomer or racemate of the obtained compound of the formula (I), wherein R stands for a methyl or ethyl group.

The intermediates used in the synthesis of compounds of the formula (I) are known substances, a part of which are commercially available.

2-Chloro-5-(2-chloro-4-trifluoromethylphenoxy)benzoic acid and its acid chloride can be prepared according to the U.S. Pat. No. 3,957,852. The (RS) and (S)-lactic acids, their methyl and ethyl esters as well as the methyl and ethyl (RS)-2-halopropionates are commercially available.

The compositions according to the invention are applied in preemergent or, more preferably, postemergent manner. The dose of the active ingredient may be varied from 10 to 500, preferably from 15 to 50 g/ha, dependently on the quality of the soil, weather conditions, components of the weed flora and the like. 50 to 1000 liters/hectare (hereinafter abbreviated: l/ha), preferably 50 to 500 l/ha of spray liquid may be used.

Compositions may be formulated by methods known per se. Thus, e.g. wettable powders (WP), suspension concentrates (SC), water-miscible solution concentrates (SL), emulsifiable concentrates (EC), granules applicable without water (S), dusting powders (DP) or oily suspension concentrates (FO) may be prepared. The active ingredient mixtures can be applied in ULV forms as well. In the said compositions the mixture of the active ingredients is present in an admixture with solid or liquid carriers or diluents and optionally with other auxiliary agents. The said auxiliary agents may be e.g. surfactants, wetting agents, suspending agents, dispersing agents, emulsifiers, anti-agglomerating agents, anti-caking agents, adhesive agents, spreaders, penetration increasing agents, substances capable of maintaining or increasing the biological activity, antifoam agents etc. From the group of solid carriers and diluents the following substances can be mentioned: inactive minerals e.g. kaolin (China-clay), various kaolin types, attapulgite, montmorillonite, mica slate, pyrophillite, bentonite, diatomaceous earth or highly dispersed synthetic silicic acids, calcium carbonate, calcinated magnesium oxide, dolomite, gypsum, tricalcium phosphate, Fuller's earth. Suitable further solid carriers and diluents are ground tobacco leaf stem, wood flour etc.

Suitable liquid diluents and solvents are the following materials: water, organic solvents; mixtures of organic solvents and those formed with water e.g. methanol, ethanol, n-propanol, isopropanol, diacetone alcohol, benzyl alcohol; esters of the said alcohols e.g. methyl cellosolve; ketones e.g. dimethyl ketone, methyl ethyl ketone, methyl isobutyl ketone, cyclopentanone, cyclohexanone etc.; ethyl acetate, n- and isobutyl acetate, amyl acetate, isopropyl myristate, dioctyl phthalate, dihexyl phthalate etc.; aromatic, aliphatic and alicyclic hydrocarbons e.g. paraffin hydrocarbons, cyclohexane, kerosene, gasoline, benzene, toluene, xylene, tetralin, decalin etc.; mixtures of alkyl benzenes; chlorinated hydrocarbons e.g. trichloroethane, dichloromethane, perchloroethylene, dichloropropane, chlorobenzene etc.; lactones e.g. $\gamma$-butyrolactone etc.; lactams e.g. N-methylpyrrolidone, N-cyclohexylpyrrolidone; acid amides e.g. dimethylformamide and the like; oils of vegetable or animal origin e.g. sunflower oil, olive oil, soya oil, castor oil and the like.

The suitable wetting, dispersing, emulsifying, adhesive, anti-aggregating, anti-caking and spreading agents may be of ionic or non-ionic character. The ionic surfactants may be e.g. salts of various saturated or unsaturated carboxylic acids; sulfonates of aliphatic, aromatic or arylaliphatic hydrocarbons; sulfates of alkyl, aryl or aralkyl alcohols; sulfonates of alkyl, aryl or aralkyl acids, esters and ethers; sulfonates of condensation products of phenol, cresol and naphthalene; sulfated vegetable and animal oils; alkyl, aryl and aralkyl phosphate esters; salts of the above compounds formed with alkaline or alkaline earth metals or organic bases (e.g. various amines, alkanolamines and the like. As preferred representatives of the above surfactants, the following compounds may be mentioned: sodium lauryl sulfate, sodium 2-ethylhexyl sulfate, sodium, ethanolamine, diethanolamine, triethanolamine, and isopropylamine salt of dodecylbenzenesulfonic acid; sodium mono- and diisopropylnaphthalene sulfonate; sodium salt of naphthalenesulfonic acid, sodium diisooctylsulfosuccinate; sodium xylenesulfonate; sodium or calcium salt of petroleumsulfonic acid; soaps; potassium, sodium, calcium, aluminum, magnesium stearate and the like. The phosphate esters may be e.g. ethers of phosphatized alkyl phenols or fatty alcohols formed with polyglycols and forms thereof partially or completely neutralized with the cations or organic bases mentioned above. As further suitable representatives of anionic surfactants, disodium N-octadecylsulfosuccinate, sodium N-oleyl-N-methyl-tauride and various lignin sulfonates can be mentioned.

Suitable non-ionic wetting, dispersing and emulsifying agents are the ethers of ethylene oxide formed with $C_{10-20}$ alcohols, e.g., stearyl polyoxyethylene, oleyl, polyoxyethyelene and the like; ethers formed with alkylphenols e.g. polyglycol ethers formed with tertiary butyl-, octyl and nonylphenol etc.; esters of various acids e.g. polyethylene glycol ester of stearic acid or myristic acid or polyethylene glycol oleate etc.; block polymers of ethylene oxide and propylene oxide; partial esters of fatty and oleic acids formed with hexitol anhydrides; esters of sorbitol formed with oleic acid or stearic acid; condensation products of the above compounds formed with ethylene oxide; tertiary glycols e.g. 3,6-dimethyl-4-octyne-3,6diol or 4,7-dimethyl-5-decyne-4,7-diol; polyethylene glycol thioethers, e.g. ester of dodecyl mercapton formed with polyethylene glycol, etc.

As adhesive agents, e.g. alkaline earth metal soaps; salts of sulfosuccinic acid ester; natural or artificial, water-soluble macromolecules e.g. casein, starch, Arabian gum, cellulose ethers, methylcellulose, hydroxycellulose, polyvinylpyrrolidone and polyvinyl alcohol etc. may be used.

Suitable antifoam agents are lower polyoxyethylene and polyoxypropylene block polymers (wherein the number of octyl-, nonly- and phenylpolyoxyethylene/ethylene oxide units is $>5$); long-chain alcohols e.g. octyl alcohol, special silicone oils etc.

By using suitable additives, formulated compositions of the present invention can be made colloid-chemically compatible with various fertilizers.

The selective herbicidal compositions of the present invention may comprise known pesticides and/or nutritive components, if necessary.

Wettable powders (WP) can be prepared e.g. by mixing the active ingredient(s), auxiliary agent(s) and surfactant(s) with the carriers, then grinding and finally homogenizing the mixture. Liquid surfactants may be applied e.g. by spraying them on the solid organic or inorganic carrier(s) or onto a powder mixture comprising the solid active ingredient. When a liquid surfactant is used, the previously ground solid components may be suspended in an organic solvent comprising liquid surfactants. This suspension can be dried e.g. by pulverization. Thus, the surfactant is applied onto the surface of a mixture of the solid active ingredient and the solid diluent.

A self-emulsifiable liquid, suitable for the preparation of aqueous dispersed emulsions (so-called emulsifiable concentrate /EC/) can be prepared by dissolving the active ingredient or a mixture thereof in a water immiscible solvent. The emulsifiable concentrate thus obtained forms with water spontaneously or under slight mechanical effect a spray emulsion which remains unchanged and stable even after long storage.

A water-soluble solution concentrate (SL) can be prepared by dissolving the active ingredient and the suitable water-soluble auxiliary materials (additives) in water and/or in a water-miscible solvent. After diluting with water, a spray liquid with the desired concentration can be obtained. The aqueous solution concentrate of the active ingredient may be dispersed also in a water-immiscible liquid by choosing (selecting) a suitable emulsifying agent to obtain a so-called "inverse" emulsion. Thus, by the convenient selection of the solvent and surface active agents, such compositions can be prepared which, on the effect of mixing with water or water-immiscible liquids, result in even molecularly dispersed phases remaining unchanged even after a long time (of storage).

A suspension concentrate (SC) can be prepared by dissolving the wetting and dispersing agents in a mixture of water (preferably) ion-exchanged water) and an antifoam component (preferably ethylene glycol or glycerol), if necessary under warming. To the solution thus obtained a mixture of the solid (powdered or crystalline) active ingredients is added under continuous stirring and, if desired, an anti-caking component is added. The slurry thus obtained (solid particles - liquid phase) is ground in a wet mill (e.g. a closed Dyno mill) to the desired particle size, preferably to a maximum particle size of 5 μm. After grinding, an antifoam agent and a thickening component are added under homogenization. Alternatively, the order of succession of the addition of the components may be changed or further agents (e.g. dyes) may be added. In addition to the active ingredient according to present invention other active ingredients may be used as combination partners.

Solid active ingredients having a low melting point may also be introduced in the form of a melt without or together with an emulsifier.

ULV compositions can be formulated similarly to EC (or in certain cases to SC) compositions.

Granules suitable for direct use (G) can be prepared by extrusion, lamination, by applying onto a granular carrier (e.g. ground limestone) or by absorbing a liquid component in a carrier having sorption capacity.

Granules applicable for spraying purposes (WG) can be prepared starting from WP and/or SC with the aid of an agglomeration technology e.g. in a dragee pan by using a binding agent.

A spray or dusting powder suitable for use in agriculture can be obtained from the above compositions by known methods by dilution with water or an inert solid carrier. The active ingredient content of the said ready-for-use compositions is generally below 5% by weight, preferably 0.01–3% by weight.

In the compositions to be used (applied), the amount of the active ingredient may be varied within wide limits; it essentially depends on the effect desired.

SPECIFIC EXAMPLES

The invention is illustrated in detail by the following non-limiting Examples.

In the $^1$h—NMR and $^{13}$C—NMR spectroscopic data given in the Examples, the identification method indicated in the formula (IV)

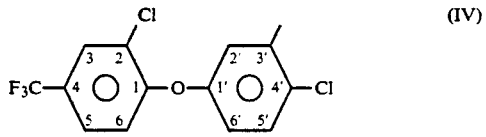

(IV)

was used. Although this is different from the indication according to the nomenclature, however, it makes it possible to carry out an uniform spectroscopic evaluation.

EXAMPLE 1

Preparation of (S)-1'-methoxycarbonylethyl 2-chloro-5-(2-chloro-4-trifluoromethylphenoxy)-benzoate (compound No. 1)

23.2 g (0.2229 mol) of methyl (S)-lactate $[[\alpha]_{20}^D = -8.97°$ (neat)], 18.1 ml (0.2229 mol) of pyridine and 100 ml of anhydrous benzene are weighed in a three-necked flask equipped with a dropping funnel and a reflux condenser. The mixture is cooled to 10° C. and a solution containing 82.25 g (0.2229 mol) of 2-chloro-5-(2-chloro-4-trifluoromethylphenoxy)benzoyl chloride in 100 ml of benzene is dropwise added under stirring. The reaction is strongly exothermic thus, the addition should be regulated in such a way that the temperature of the reaction mixture remains at 10° to 20° C. by external cooling. After this addition, the suspension is stirred at room temperature for 3 hours, then successively washed twice with 100 ml of 3% hydrochloric acid each, then with 100 ml of 3% sodium hydrogen carbonate solution and finally with 100 ml of water. The benzene layer is dried over anhydrous magnesium sulfate, then benzene is evaporated under the pressure of the water jet pump to give the named compound in the form of an oily product in a yield of 73.3 g (75.2%).
Molecular weight: 436.9
Color and form: pale yellow oil.
$[\alpha]_{20}^D = +14.16°$ (c 3.39, benzene)
$n_{20}^D = 1.5310$ The characteristic fragments of the mass spectrum of the product are as follows:

m/e
(r.i.) = 436(230) = F$_3$C(CL)C$_6$H$_3$OC$_6$H$_3$(Cl)COOCH(CH$_3$)COOCH$_3$

333(1000) = F$_3$C(Cl)C$_6$H$_3$OC$_6$H$_3$(Cl)CO $^1$H—NMR(CDCl$_3$): δ1.53(d, 3H), 3.70 (s, 3H), 5.27 (q, 1H), 6.88–7.68 ppm (complex m, 6H).
$^{13}$C—NMR (CDCL$_3$): δ155.0 (s, C-1), 132.8 (s, C-2), 128.5 (q, $^3$J (FCCC)=3.6 Hz, C-3), 125.5 (q, $^3$J (FCCC)=3.6 Hz, C-5), 119.8 (s, C-6), 122.45 (q, J (FC)=238 Hz, CF$_3$), 154.2 (s, C-1'), 122.0 (s, C-2'), 131. (s, C-3'), 129.5 (s, C-4'), 126.1 (s, C-5'), 123.1 (s, C-6'), 170.8 (s, COOCH), 164.0 (s, COOCH$_3$) 52.5 (s, OCH$_3$), 16.9 (s, CH$_3$), 70.0 ppm (s, CH).

EXAMPLE 2

Preparation of (RS)-1'-methoxycarbonylethyl 2-chloro-5-(2-chloro-4-trifluoromethylphenoxy)benzoate (compound No. 2)

20 g (0.1921 mol) of methyl (RS)-lactate, 21.3 g (0.2113 mol) of triethylamine and 100 ml of anhydrous toluene are weighted in a three-tube bottle equipped with a stirrer, dropping funnel and reflux condenser. After cooling the reaction mixture to 0° to 10° C., a solution containing 70.9 g (0.1921 mol) of 2-chloro-5-(2-chloro-4-trifluoromethylphenoxy)benzoyl chloride in 100 ml of toluene is dropwise added while stirring. After this addition, the suspension is stirred at 20° to 30° C. for 3 hours, then successively washed twice with 100 ml of 3% hydrochloric acid each saturated with sodium chloride, then with 100 ml of 3% sodium hydrogen carbonate solution saturated with sodium chloride and finally with water. After drying the toluene solution over anhydrous magnesium sulfate, toluene is evaporated under the pressure of the water jet pump to give the named compound as a pale yellow oil in a yield of 80.2 g (95.6%).
Molecular weight: 436.9
Color and form: pale yellow oil
$n_{20}{}^D = 1.5305$ The characteristic fragments of the mass spectrum of the product are as follows:

m/e (r. i.) = 436
(230) = $F_3C(Cl)C_6H_3OC_6H_3(Cl)COOCH(CH_3)COOCH_3$ 333 (1000) = $F_3C(Cl)C_6H_3OC_6H_3(Cl)CO$ $^1H$—NMR (CDCl$_3$): δ1.53 (d, 3H), 3.70 (s, 3H), 5.27 (q, 1H), 6.88–7.68 ppm (complex m, 6H).
$^{13}C$—NMR (CDCL$_3$): δ155.0 (s, C-1), 132.8 (s, C-2), 128.5 (q, $^3J$ (FCCC) = 3.6 Hz, C-3), 125.5 (q, $^3J$ (FCCC) = 3.6 Hz, (c-5), 119.8 (s, C-6), 122.45 (q, J (FC) = 238 Hz, CF$_3$ 154.2 (s, C-1'), 122.0 (s, C-2'), 131 (s, C-3'), 129.5 (s, C-4'), 126.1 (s, C-5'), 123.1 (s, C-6'), 170.8 (s, COOCH), 164.0 (s, COOCH$_3$), 52.5 (s, OCH$_3$), 16.9 (s, CH$_3$), 70.0 ppm (s, CH).

EXAMPLE 3

Preparation of (S)-1'-ethoxycarbonylethyl 2-chloro-5-(2-chloro-4-trifluoromethylphenoxy)benzoate (compound No. 3)

48.3 ml (0.426 ml) of ethyl (S)-lactate [[α]$_{20}{}^D$ = −12.0° (neat)], 150 ml of benzene and 34.5 ml (0.426 mol) of pyridine are weighed in a three-tube bottle equipped with a stirrer, dropping funnel and reflux condenser. After cooling the homogeneous solution to 10° C., a solution containing 157.2 g (0.426 mol) of 2-chloro-5-(2-chloro-4-trifluoromethylphenoxy)-benzoyl chloride in 300 ml of benzene is dropwise added while maintaining the temperature of the reaction mixture between 10° and 20° C. by external cooling. After stirring the reaction mixture at 20° to 30° C. for additional 12 hours, 200 ml of 3% hydrochloric acid are added to the suspension and after a short stirring, the benzene layer is separated. After successively washing the organic phase twice with 200 ml of 3% hydrochloric acid solution each, then with 200 ml of 3% sodium carbonate solution and finally twice with 200 ml of water each, the benzene solution is dried over magnesium sulfate. The most part of the solvent is distilled off under atmospheric pressure and the residual solvent is removed by using a water jet pump. The named compound is obtained as yellow oil in a yield of 175 g (91.1%).
Molecular weight: 450.9
Color and form: yellow oil
[α]$_{20}{}^D$ = +12.72° (c 5.975, benzene)
$n_{20}{}^D = 1.5267$ The characteristic fragments of the mass spectrum of the product are as follows:

m/e (r. i.) = 450
(270) = $F_3C(cl)C_6H_3OC_6H_3(CL)COOCH(CH_3)COOC_2H_5$ 333 (1000) = $F_3C(CL)C_6H_3OC_6H_3(Cl)CO$ 270 (100) = $F_3C(Cl)C_6H_3OC_6H_3$ $^1H$—NMR (CDCl$_3$): δ1.17 (tr,, 3H), 1.51 (d, 3H), 4.13 (q, 2H), 5.20 (q, 1H), 6.87–7.65 ppm (complex m, 6H).

$^{13}C$—NMR (CDCl$_3$): δ154.3 (s, c-1), 132.8 (s, C-2), 128.4 (q, $^3J$ (FCCC) = 3.6 Hz, C-3), 125.5 (q, $^3J$(FCCC) = 3.6 Hz, C-5), 119.9 (s, C-6), 122.4 (q, J(FC) = 238 Hz CF$_3$), 154.3 (s, C-1'), 122.0 (s, C-2'), 131.2 (s, C-3'), 129.4 (s, C-4'), 126.1 (s, C-5'), 123.1 (s, C-6'), 170.3 (s, COOCH), 164.0 (s, COOCH$_2$CH$_3$), 61.6 (s, OCH$_2$), 14.1 (s, CH$_2$CH$_3$), 16.9 (s, CH$_3$), 70.1 ppm (s, CH).

EXAMPLE 4

Preparation of (RS)-1'-ethoxycarbonylethyl 2-chloro-5-(2-chloro-4-trifluoromethylphenoxy)benzoate (compound No. 4)

60 g (0.1709 mol) of 2-chloro-5-(2-chloro-4-trifluoromethylphenoxy)benzoic acid, 250 ml of benzene, 28.1 g of DBU (0.1709 mol, a substance of 93%) and 22.1 ml (0.1709 mol) of ethyl 2-bromopropionate are weighed in a three-tube bottle equipped with a stirrer, dropping funnel and reflux condenser. The reaction mixture is heated to the boiling point and refluxed for 14 hours. After cooling down, the reaction mixture is successively washed with 50 ml of 3% hydrochloric acid, then with 50 ml of 3% sodium hydroxide solution and finally twice with 50 ml of water each. After drying of the organic phase over magnesium sulfate, the solvent is removed first under atmospheric pressure and then under reduced pressure to obtain the named compound as a yellow oil in a yield of 75.4 g (87.6%).
Molecular weight: 450.9
Color and form: yellow oil
$n_{20}{}^D = 1.5261$ The characteristic fragments of the mass spectrum of the product are as follows:

m/e (r. i.) = 450
(270) = $F_3C(Cl)C_6H_3OC_6H_3(Cl)COOCH(CH_3)COOC_2H_5$ 333 (1000) = $F_3C(Cl)C_6H_3OC_6H_3(Cl)CO$ 270 (100) = $F_3C(Cl)C_6H_3OC_6H_3$ $^1H$—NMR(CDCl$_3$): δ1.17 (t, 3H), 1.51 (d, 3H), 4.13 (q, 2H), 5.20 (q, 1H), 6.87–7.65 ppm (complex m, 6H).
$^{13}C$—NMR (CDCL$_3$): δ154.3 (s, C-1), 132.8 (s, C-2), 128.4 (q, $^3J$(FCCC) = 3.6 Hz, C-3), 125.5 (q, $^3J$(FCCC) = 3.6 Hz, C-5), 119.9 (s, C-6), 122.4 (q, J(FC) = 238 Hz, CF$_3$), 154.3 (s, C-1'), 122.0 (s, C-2'), 131.2 (s, C-3'), 129.4 (s, C-4'), 126.1 (s, C-5'), 123.1 (s, C-6'), 170.3 (s, COOCH), 164.0 (s, COOCH$_2$CH$_3$), 61.6 (s, OCH$_2$), 14.1 (s, CH$_2$CH$_3$), 16.9 (s, CH$_3$), 70.1 ppm (s, CH).

EXAMPLE 5

Preparation of (R)-1'methoxycarbonylethyl-2-chloro-5-(2-chloro-4-trifluoromethylphenoxy)benzoate (Compound C)

This compound was prepared following substantially the procedure of Example 1 using methyl (R)-lactate instead of methyl (S)-lactate at a yield of 91.3%
Molecular weight: 436.9
Color and form: yellow oil
[α]$_{20}{}^D$ = −14.27° (c 3.39, benzene)
$n_{20}{}^D = 1.5310$ The characteristic fragments of the mass spectrum of the named product, the data of the $^1H$- and $^{13}C$—NMR spectra correspond to those of the (S)-enantiomer obtained in Example 1.

EXAMPLE 6

Preparation of (R)-1'-ethoxycarbonylethyl-2-5-(2-chloro-4-tri-fluoromethylphenoxy)benzoate (Compound D)

This compound was prepared following substantially the procedure given in Example 3 using ethyl (R)-lactate instead of ethyl (S) lactate at a yield of 89%.
Molecular weight: 450.9
Color and form: yellow oil
$[\alpha]_{20}^D = -13.97°$ (c 4.08, benzene)
$n_{20}^D = 1.5382$ The characteristic fragments of the mass spectrum of the named product, the data of the $^1$H— and $^{13}$C—NMR spectra correspond to those of the (S)-enantiomer obtained in Example 3.

EXAMPLE 7 a) Preparation of an emulsifiable concentrate (20 EC)

|  | % by weight |
|---|---|
| Compound No. 2 | 20 |
| 2-Ethoxyethanol | 10 |
| Cyclohexanone | 35 |
| Emulsogen El 360 (1) | 7 |
| Tensiofix CD (2) | 3 |
| Xylene | 25 |

(1) Ethoxylated castor oil
(2) Ethoxylated coconut alcohol

Emulsogen E,L 360 and Tensiofix CD 5 are dissolved in the mixture of 2-ethoxyethanol, cyclohexanone and xylene, then the active ingredient (compound No. 2) is introduced and the solution is stirred for 2 hours.

b) Preparation of an emulsifiable concentrate (35 EC)

|  | % by weight |
|---|---|
| Compound No. 3 | 35 |
| Cyclohexanone | 10 |
| Tensiofix CG 21 (1) | 2 |
| Tensiofix B 7453 (2) | 8 |
| Xylene | 45 |

(1) A mixture of ethoxylated fatty alcohol, ethoxylated nonylphenol and their phosphates
(2) A solution of calcium dodecylbenzenesulfonate, ethoxylated nonylphenol and ethoxylated-propoxylated nonylphenol in n-butanol.

The process described in Example 7a) is followed.

Compositions containing other compounds of the invention as active ingredients may similarly be prepared.

EXAMPLE 8

Preparation of microgranules

|  | % by weight |
|---|---|
| Compound No. 4 | 0.1 |
| Cyclohexanone | 5.0 |
| Bentonite | 94.9 |

A solution containing the active ingredient (compound No. 4) in cyclohexanone is sprayed onto bentonite previously ground to a particle size of 50 μ and placed in a revolving drum. The stirring is continued for 1 hour while cyclohexanone is evaporated.

Compositions containing other compounds of the invention as active ingredients may similarly be prepared.

EXAMPLE 9

Preparation of water-dispersible granules (WG)

|  | % by weight |
|---|---|
| Compound No. 1 | 50 |
| Cab-O-Sil M5 (1) | 5 |
| Atlox 4862 (2) | 3 |
| Polifon O (3) | 6 |
| Geropon IN (4) | 5 |
| Kaolin | 31 |

(1) Amorphous silicon dioxide
(2) Naphthalenesulfonate-formaldehyde condensation product
(3) Binding material (sodium ligninsulfonate)
(4) Isopropyl naphthalenesulfonate The active ingredient is mixed in a grinding mortar with amorphous silicon dioxide, Atlox 4862 dispersing agent and Geropon IN wetting agent as well as kaolin. The mixture is ground to fine particles (until the portion of the particles greater than 44 μ in diameter becomes less than 0.5%). The powder is mixed in a kneader with the aqueous solution of the Polifon O binding agent and then granules of 1 mm in diameter are prepared in an extruder. The granules are dried in air stream.

Compositions containing other compounds may similarly be prepared.

EXAMPLE 10

Biological (herbological) investigations

In this Example, the herbicidal activity and selectivity of the four compounds according to the present invention are illustrated in comparison to the structurally related (RS)-1'-ethoxycarbonylethyl 2-bromo-5-(2-chloro-4-trifluoromethylphenoxy)benzoate (compound A) and to the commercially available (RS)-1'-ethoxycarbonylethyl 5-(2-chloro-4-trifluoromethylphenoxy)-2-nitrobenzoate (compound B).

Depending on the plant species, an equal number (20 to 50) of seeds each were sowed in plastic cultivating bottles to a depth of 0.5 cm, then the soil was sprinkled when necessary and the bottles were maintained under the optimum temperature and light conditions. After the weeds had reached a real 2 to 4-leaf phase or the cultivated plants had been in a 3 to 6-leaf phase, respectively the spraying was carried out with 5, 15, 45, 135, 405 or 1215 g/ha dose, respectively of the active ingredient. The evaluation was made on the 10th day after the treatment by measuring the percentage of perishment (L. Bánki: Bioassay of Pesticides in the Laboratory, Akadémiai Kiadó, Budapest, Hungary, 1978) and determining therefrom the doses required for a weed kill in excess of 90% by using the probit analysis (D. J. Finney: Probit Analysis, Cambridge, University Press, 2nd Ed. 1964). Simultaneously, the selectivity threshold values of the cultivated plants, i.e. the highest doses tolerated by the cultivated plants without any damage, were determined. The results are summarized in Tables 1 and 2.

Abbreviations used in the Tables are as follows:

| a) *Amarantus retroflexus* | (pilous amaranth) |
|---|---|
| b) *Solanum nigrum* | (black nightshade) |
| c) *Portulaca oleraceae* | (fatty purslane) |
| d) *Matricaria inodora* | (scentless matricaria) |

-continued

| | |
|---|---|
| e) *Datura stramonium* | (medicinal nightshade) |
| f) *Chenopodium album* | (white goose-foot) |
| g) *Oryza sativa* | (rice) |
| h) *Triticum vulgare* | (winter wheat) |
| i) *Hordeum vulgare* | (winter barley) |
| j) *Glycine soja* | (soy bean) |

TABLE 1

Doses required to a herbicidal activity over 90% (g/ha)

| No or symbol of the compound | R | Configuration | Doses required to a herbicidal activity over 90%. | | | | | |
|---|---|---|---|---|---|---|---|---|
| | | | a | b | c | d | e | f |
| 1. | Me | S | 15 | 20 | 20 | 30 | 50 | 50 |
| 2. | Me | RS | 30 | 30 | 40 | 60 | 150 | 150 |
| 3. | Et | S | 20 | 25 | 20 | 40 | 50 | 50 |
| 4. | Et | RS | 40 | 35 | 40 | 65 | 150 | 450 |
| Compound A | Et | RS | 50 | 100 | 55 | 120 | 200 | 500 |
| Compound B | Et | RS | 50 | 100 | 50 | 130 | 250 | 500 |
| Compound C | Me | R | 60 | 100 | 60 | 120 | 220 | 500 |
| Compound D | Et | R | 60 | 100 | 55 | 125 | 200 | 500 |

TABLE 2

Selectivity threshold values of cultivated plants (g/ha)

| No. or symbol of the compound | R | Configuration | Selectivity threshold values (g/ha) | | | |
|---|---|---|---|---|---|---|
| | | | g | h | i | j |
| 1. | Me | S | 200 | 150 | 150 | 100 |
| 2. | Me | RS | 250 | 200 | 150 | 100 |
| 3. | Et | S | 250 | 200 | 150 | 100 |
| 4. | Et | RS | 300 | 250 | 200 | 100 |
| Compound A | Et | RS | 190 | 50 | 60 | 60 |
| Compound B | Et | RS | 150 | 75 | 50 | 30 |
| Compound C | Me | R | 250 | 200 | 150 | 100 |
| Compound D | Et | R | 250 | 250 | 200 | 100 |

EXAMPLE 11

Field experiments

These investigations were carried out by using the compounds Nos. 1, 2, 3 and 4, respectively, according to the invention and the reference compounds A, B, C and D respectively on winter wheat of the Aurora species on parcels of 20 m² in four repetitions. The compounds used in these experiments were formulated as described under a) in Example 7. The weeds occurring in the areas indicated were: Anthemis arvensis, Convolvulus arvensis, Matricaria inodora, Veronica hederifolia and Stellaria media. The spraying was carried out on March 23, when Stellaria media reached the beginning of the blooming and other weeds were in a development phase of at most 10 cm. The herbicidal activity of the compositions was evaluated at the end of the 3rd week after spraying (L. Bánki: Bioassay of Pesticides in the Laboratory, Akadémiai Kiadó, Budapest, Hungary, 1978). Except of Stellaria media, 100% of the weeds were killed in all treatments. An important difference concerning the herbicidal efficiency on Stellaria media was observed between the compounds according to the invention and the reference compounds. Stellaria media was advantageously killed by the compounds according to the invention whilst the reference substances were inactive. The covering by Stellaria media of the fields treated by a 50 g/ha dose of the reference substances reached 50%. A considerable difference exists between the phytotoxicity against the winter wheat of the compounds according to the invention and that of the reference compounds.

The data obtained on winter wheat and Stellaria media are summarized in Table 3.

TABLE 3

Effect on the winter wheat and *Stellaria media*

| No. or symbol of the compound | Dose g/ha | R | Configuration | Perishment % | |
|---|---|---|---|---|---|
| | | | | Winter wheat | Stellaria media |
| 1 | 25 | Me | S | 0 | 65 |
| | 50 | | | 0 | 100 |
| | 100 | | | 0 | 100 |
| 2 | 25 | Me | RS | 0 | 45 |
| | 50 | | | 0 | 100 |
| | 100 | | | 0 | 100 |
| 3 | 25 | Et | S | 0 | 70 |
| | 50 | | | 0 | 100 |
| | 100 | | | 0 | 100 |
| 4 | 25 | Et | RS | 0 | 50 |
| | 50 | | | 0 | 90 |
| | 100 | | | 0 | 100 |
| Compound A | 25 | Et | RS | 0 | 0 |
| | 50 | | | 0 | 0 |
| | 100 | | | 15 | 0 |
| Compound B | 25 | Et | RS | 0 | 0 |
| | 50 | | | 0 | 0 |
| | 100 | | | 10 | 0 |
| Compound C | 25 | Me | R | 0 | 0 |
| | 50 | | | 0 | 0 |
| | 100 | | | 25 | 0 |
| Compound D | 25 | Et | R | 0 | 0 |
| | 50 | | | 0 | 0 |
| | 100 | | | 20 | 0 |

We claim:

1. (S) enantiomer or racemate of a compound of the formula (I),

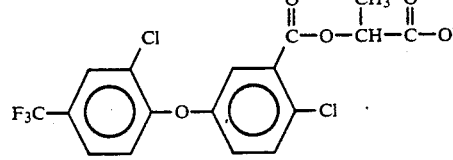

wherein R is a methyl or ethyl group.

2. (S) enantiomer of a compound of the formula (I), as claimed in claim 1 wherein R is a methyl group.

3. Racemate of a compound of the formula (I), as claimed in claim 1 wherein R is a methyl group.

4. (S) enantiomer of a compound of the formula (I) as claimed in claim 1 wherein R is an ethyl group.

5. Racemate of a compound of the general formula (I) as claimed in claim 1 wherein R is an ethyl group.

6. A herbicide composition, which comprises the (S) enantiomer or racemate of a compound of the formula (I),

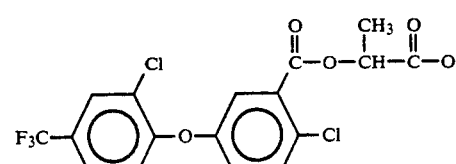

wherein R is a methyl or ethyl group, as active ingredient in an amount of 0.01 to 95% by weight together with at least one agriculturally inert carrier.

7. A composition as claimed in claim 6 which comprises (S)-1'-methoxy-carbonylethyl 2-chloro-5-(2- chloro-4-trifluoromethylphenoxy)benzoate as an (S) enantiomer of the formula (I).

8. A composition as claimed in claim 6 which comprises (RS)-1'-methoxycarbonylethyl 2-chloro-5-(2-chloro-4-trifluoromethylphenoxy)benzoate as a racemate of the formula (I).

9. A composition as claimed in claim 6 which comprises (S)-1'-ethoxycarbonylethyl 2-chloro-5-(2-chloro-4-trifluoromethylphenoxy)benzoate as an (S) enantiomer of the formula (I).

10. A composition as claimed in claim 6 which comprises (RS)-1'-ethoxycarbonylethyl 2-chloro-5-(2-chloro-4-trifluoromethylphenoxy)benzoate as a racemate of the formula (I).

11. A method of controlling undesired weed growth comprising applying a herbicidally effective amount of a compound as claimed in claim 1 to the plant or soil pre emergence or post emergence.

* * * * *